US005547965A

United States Patent [19]
Krüger et al.

[11] Patent Number: 5,547,965
[45] Date of Patent: Aug. 20, 1996

[54] USE OF SUBSTITUTED AMINES FOR THE TREATMENT OF BRAIN FUNCTION DISORDERS

[75] Inventors: Bernd-Wieland Krüger, Bergisch Gladbach, Germany; Fritz Maurer, Oyama, Japan; Christoph Methfessel, Sprockhövel, Germany; Klaus Tietjen, Langenfeld, Germany; Alfred Maelicke, Niederholm, Germany; Bernard Schmidt, Lindlar, Germany; Kozo Shiokawa, Kawasaki, Japan

[73] Assignee: Bayer Aktiengesellschaft, Leverkusen, Germany

[21] Appl. No.: 424,950

[22] Filed: Apr. 19, 1995

[30] Foreign Application Priority Data

Apr. 27, 1994 [DE] Germany ............... 44 14 569.1

[51] Int. Cl.$^6$ ............... A61K 31/44; A61K 31/53; A61K 31/445; A61K 31/415
[52] U.S. Cl. ............... 514/342; 514/245; 514/318; 514/341; 514/357; 514/400
[58] Field of Search ............... 514/342, 245, 514/318, 341, 357, 400

[56] References Cited

U.S. PATENT DOCUMENTS

| | | | |
|---|---|---|---|
| 4,531,002 | 7/1985 | Harris | 514/375 |
| 4,590,272 | 5/1986 | Shiokawa et al. | 544/335 |
| 4,647,570 | 3/1987 | Shiokawa et al. | 514/341 |
| 4,687,845 | 8/1987 | Hollowood et al. | 544/54 |
| 4,806,553 | 2/1989 | Shiokawa et al. | 514/332 |
| 4,812,454 | 3/1989 | Shiokawa et al. | 514/256 |
| 4,812,571 | 3/1989 | Shiokawa et al. | 514/342 |
| 4,849,432 | 7/1989 | Shiokawa et al. | 514/341 |
| 4,914,113 | 4/1990 | Shiokawa et al. | 514/333 |
| 4,918,086 | 4/1990 | Gsell | 514/351 |
| 4,918,088 | 4/1990 | Gsell | 514/357 |
| 4,948,798 | 8/1990 | Gsell | 514/275 |
| 4,963,572 | 10/1990 | Gsell | 514/357 |
| 4,963,574 | 10/1990 | Bachmann et al. | 514/357 |
| 4,988,712 | 1/1991 | Shiokawa et al. | 514/340 |
| 5,034,404 | 7/1991 | Uneme et al. | 514/365 |
| 5,034,524 | 7/1991 | Shiokawa et al. | 514/124 |
| 5,039,686 | 8/1991 | Davies et al. | 514/341 |
| 5,049,571 | 9/1991 | Gsell | 514/345 |
| 5,166,164 | 11/1992 | Nanjo et al. | 514/357 |
| 5,175,301 | 12/1992 | Minamida et al. | 514/357 |
| 5,192,778 | 3/1993 | Kodaka et al. | 514/341 |
| 5,204,359 | 4/1993 | Shiokawa et al. | 514/332 |
| 5,204,360 | 4/1993 | Shiokawa et al. | 514/342 |
| 5,238,949 | 8/1993 | Shiokawa et al. | 514/327 |
| 5,256,679 | 10/1993 | Minamida et al. | 546/272 |
| 5,280,123 | 1/1994 | Nanjo et al. | 514/365 |
| 5,304,566 | 4/1994 | Ishimitsu et al. | 514/357 |
| 5,384,324 | 1/1995 | Shiokawa et al. | 514/365 |

FOREIGN PATENT DOCUMENTS 0428941  5/1991  European Pat. Off. .
9117659  5/1991  WIPO .

OTHER PUBLICATIONS

D. Collerton, Neurosscience, vol. 19, pp. 1–28, 1986.
R. T. Bartus, et al., Science, vol. 217, pp. 408–417, 1982.
P. T. Francis, et al., New England J. Med., vol. 313, pp. 7–11, 1985.
K. J. Kellar, et al., Brain Res., vol. 436, pp. 62–68, 1987.
A. Nordberg, et al., Neurosci. Letters, vol. 86, pp. 317–321, 1988.
E. Giacobini, J. Neurosci. Res., vol. 27, pp. 548–560, 1990.
A. Nordberg, et al., Neurosci. Letters, vol. 86, pp. 747–758, 1992.
D. D. Flynn, et al., J. Neurochemistry, vol. 47, pp. 1948–1954, 1986.
M. W. Decker, et al., Brain Res., vol. 572, pp. 281–285, 1992.
S. Poincheval–Fuhrman, et al., Pharmacology, vol. 4, pp. 535–539 (1993).
E. D. Levin, et al., Cognitive Brain Res., vol. 1, pp. 137–143, 1993.
M. W. Decker, et al., Pharmacol. Biochem. Behav., vol. 45, pp. 571–576, 1993.
A. V. Terry, et al., Pharmacol. Biochem. Behav., vol. 45, pp. 925–929, 1993.
D. G. Linville, et al., J. Pharmacol. Exp. Ther., vol. 267, pp. 440–448, 1993.
P. A. Newhouse, et al., Psychopharmacology, vol. 95, pp. 171–175, 1988.
B. Sahakian, Br. J. Psychiatry, vol. 154, pp. 797–800, 1989.
DSM III–R, American Psychiatric Association, APA Press, Washington, D.C., 1987.
J. D. Brioni, et al., Eur. J. Pharmacol., vol. 238, pp. 1–8, 1993.
E. C. Hulme, Editor, Receptor–Ligand Interactions, Oxford University Press, pp. 1–458, 1992.
T. Chard, An Introduction to Radioimmunoassay and Related Techniques; Elsevier, Amsterdam, statistische Auswertung per Computer, pp. 163–171, 1990.
Derwent Abstract of JP 03–220,176, (Sep. 27, 1991).
Derwent Abstract of JP 03–255,072, (Nov. 13, 1991).
Derwent Abstract of JP 03–279,359, (Dec. 10, 1991).
Derwent Abstract of JP 03–246,283, (Nov. 1, 1991).
Derwent Abstract of JP 63–287,764, (Nov. 24, 1988).
Derwent Abstract of JP 63–07,857, (Dec. 15, 1988).
Derwent Abstract of JP 02–207,083 (Aug. 16, 1990).

*Primary Examiner*—Raymond Henley, III
*Attorney, Agent, or Firm*—Sprung Horn Kramer & Woods

[57] ABSTRACT

The invention relates to the use of substituted amines for the treatment and prevention of brain function disorders. The substituted amines are suitable on the basis of their properties as agonistic or antagonistic ligands for nicotinergic receptors, in particular for the treatment and prevention of senile and presenile dementia and dementia of the Alzheimer type, and of depressions.

13 Claims, No Drawings

USE OF SUBSTITUTED AMINES FOR THE TREATMENT OF BRAIN FUNCTION DISORDERS

The invention relates to the use of substituted amines having an agonistic or antagonistic effect on nicotinergic receptors for the treatment and prevention of brain function disorders, suitable pharmaceutical compositions and their preparation.

It is known that the neurotransmitter acetylcholine plays an important part in the regulation of learning and memory processes in the brain (R. T. Bartus et al., Science 217: 408, 1982; D. Collerton, Neuroscience 19: 1, 1986). Cognitive brain function disorders, such as occur, for example, in old age or in primary degenerative disorders, are accompanied by a decrease in cholinergic neurotransmission (P. T. Francis et al., New England J. Med. 313: 7, 1985). The function of nicotinic acetyl-choline receptors in the brain is particularly affected in this case (K. K. Kellar, Brain Res. 436: 62, 1987; A. Nordberg et al., Neurosci. Letters 86: 317, 1988; E. Giacobini, J. Neurosci. Res. 27: 548, 1990 A. Nordberg et al., Neurobiol. Aging 13: 747, 1992). This deficit is restricted here to the presynaptic nicotine receptors, while the expression of post-synaptic receptors remains unaffected (D. D. Flynn and D. C. Mash, J. Neurochemistry 47: 1948, 1986).

After administration of nicotine or selective nicotine receptor agonists, positive effects on learning and memory were found in animal experiments (M. W. Decker et al., Brain Res. 5672: 281, 1992; S. Poincheval-Fuhrman and S. J. Sara, Behav. Pharmacology 4: 535, 1993; E. D. Levin et al., Cognitive Brain Res. 1: 137, 1993; M. W. Decker et al., Pharmacol. Biochem. Behav. 45: 571, 1993; A. V. Terry et al., Pharmacol. Biochem. Behav. 45: 925, 1993). It is additionally known that nicotine promotes the cerebral circulation in rats (D. G. Liniville et al., J. Pharmacol. Exp. Ther. 267: 440, 1993). Cognitive-stimulating effects of nicotine were also confirmed in clinical studies in Alzheimer patients (P. A. Newhouse et al., Psychopharmacology 95: 171, 1988; B. Sahakian, Br. J. Psychiatry 154: 797, 1989).

It is therefore suspected that pharmaceuticals having a specific effect on nicotinic receptors are suitable for the treatment and prevention of dementias classified according to the Diagnostic and Statistical Manual III (DSM III-R, American Psychiatric Association, APA Press, Washington D.C., 1987), in particular of senile and presenile dementia, dementia of the Alzheimer type, multiinfarct dementia, AIDS-related dementia, dementia in Down's syndrome, disorders of cholinergic and dopaminergic neurotransmision such as in Parkinson's and Huntington's disease, and brain function disorders as a result of infarct processes or brain trauma.

In addition to learning- and memory-enhancing effects, anxiolytic properties of nicotine receptor agonists have also been described (J. D. Brioni et al., Eur. J. Pharmacol. 238: 1, 1993). Moreover, after chronic administration nicotine potentiates the physiological effect of dopamine. On this is based the assumption that nicotinic receptor agonists are also suitable for the treatment and prevention of pathological anxiety states and depressions.

It has now been found that substituted amines of the formula (I)

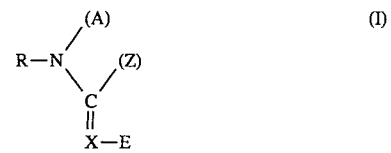

in which
R represents hydrogen, or optionally substituted acyl, alkyl, aryl, aralkyl, heteroaryl or heteroarylalkyl radicals;
A represents a monofunctional group of the hydrogen, acyl, alkyl or aryl series or represents a bifunctional group which is linked to the radical Z;
E represents an electron-withdrawing radical;
X represents the —CH= or =N— radicals, it being possible for the —CH= radical to be linked to the Z radical instead of an H atom;
Z represents a monofunctional group of the alkyl, —O—R, —S—R or

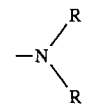

series or represents a bifunctional group which is linked to the A radical or the X radical,
stimulate nicotinic receptors of the central nervous system and can thus be employed for the treatment and prevention of brain function disorders and depressive disorders.

On the basis of the experimental results, the compounds of the formula (I) are suitable for the treatment and prevention of disorders of the dementia type and neurological disorders (e.g. senile and presenile dementia, dementia of the Alzheimer type) and also of depressions.

Preferred compounds of the formula I are those in which the radicals have the following meaning:
R represents hydrogen as well as optionally substituted radicals of the acyl, alkyl, aryl, aralkyl, heteroaryl or heteroarylalkyl series.

Acyl radicals which may be mentioned are formyl, alkylcarbonyl, arylcarbonyl, alkylsulfonyl, arylsulfonyl or (alkyl) (aryl)phosphoryl, which in turn can be substituted. Alkyl which may be mentioned is $C_{1-10}$-alkyl, in particular $C_{1-4}$-alkyl, specifically methyl, ethyl, i-propyl or sec- or t-butyl, which in turn can be substituted.

Aryl which may be mentioned is phenyl or naphthyl, in particular phenyl.

Aralkyl which may be mentioned is phenylmethyl or phenethyl.

Heteroaryl which may be mentioned is heteroaryl having up to 10 ring atoms and N, O or S, in particular N, as heteroatoms. Thiophenyl, furyl, thiazolyl, imidazolyl, pyridyl and benzothiazolyl may be mentioned specifically.

Heteroarylalkyl radicals which may be mentioned are heteroarylmethyl, heteroarylethyl having up to 6 ring atoms and N, O or S, in particular N, as heteroatoms.

Substituents which may be mentioned by way of example and preferably are:
Alkyl preferably having 1 to 4, in particular 1 or 2, carbon atoms, such as methyl, ethyl, n- and i-propyl and n-, i- and t-butyl; alkoxy preferably having 1 to 4, in particular 1 or 2, carbon atoms, such as methoxy, ethoxy, n- and i-propoxy and n-, i- and t-butoxy; alkylthio preferably having 1 to 4, in particular 1 or 2, carbon atoms, such as methylthio, ethylthio, n- and i-propylthio and n-, i- and t-butylthio; halogenoalkyl preferably having 1 to 4, in particular 1 or 2, carbon atoms and preferably 1 to 5, in particular 1 to 3, halogen atoms, the halogen atoms being identical or different and, as halogen atoms, preferably being fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino preferably having 1 to 4, in particular 1 or 2 carbon atoms per alkyl group, such as methylamino, methyl-ethyl-amino, n- and i-propylamino and methyl-n-butylamino; carboxyl; carbalkoxy preferably having 2 to 4, in particular 2 or 3, carbon atoms, such as carbomethoxy and carboethoxy; sulfo (—$SO_3$—); alkylsulphonyl preferably having 1 to 4, in particular 1 or 2 carbon atoms, such as methylsulphonyl and ethylsulphonyl; arylsulphonyl preferably having 6 or 10 aryl carbon atoms, such as phenylsulphonyl, and heteroarylamino and heterarylalkylamino such as chloropyridylamino and chloropyridylmethylamino.

A represents hydrogen and optionally substituted radicals of the acyl, alkyl or aryl series, which preferably have the meanings given above. A also represents a bifunctional group. Optionally substituted alkylene having 1–4, in particular 1–2, C atoms may be mentioned, the substituents itemized further above being mentioned as substituents.

A and Z, together with the atoms to which they are bonded, can form a saturated or unsaturated heterocyclic ring. The heterocyclic ring can contain a further 1 or 2 identical or different heteroatoms and/or hetero groups. Heteroatoms are preferably oxygen, sulphur or nitrogen and hetero groups are N-alkyl, the alkyl or the N-alkyl group preferably containing 1 to 4, in particular 1 or 2, carbon atoms. Alkyl radicals which may be mentioned are methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethylene-imine, morpholine and N-methylpiperazine.

E represents an electron-withdrawing radical, $NO_2$, CN, halogenoalkylcarbonyl such as 1,5 halogeno-$C_{1-4}$-carbonyl, in particular $COCF_3$, being mentioned in particular.

X represents —CH= or —N=.

Z represents optionally substituted alkyl, —OR, —SR, or —NRR radicals, R and the substituents preferably have the meaning given above.

Z, together with the atom to which it is bonded and the

radical in place of X, can form a saturated or unsaturated heterocyclic ring. The heterocyclic ring can contain a further 1 or 2 identical or different hetero atoms and/or hetero groups. Hetero atoms are preferably oxygen, sulphur or nitrogen and hetero groups are N-alkyl, the alkyl or the N-alkyl group preferably containing 1 to 4, in particular 1 or 2, carbon atoms. Alkyl radicals which may be mentioned are methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethylene-imine, morpholine and N-methylpiperazine.

Compounds which can be used particularly preferably according to the invention are compounds of the general formulae (II) and (III):

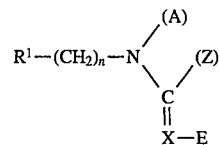

in which $R^1$ represents optionally substituted pyridin-3-yl, substituents which may be mentioned preferably being $C_1$–$C_4$-alkyl, $C_1$–$C_4$-alkoxy and halogen, such as, for example, methyl, methoxy and chlorine;

n represents 1 or 2;

A, Z, X and E have the meaning given above;

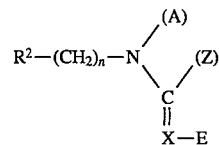

in which $R^2$ represents optionally substituted 1,3-thiazol-5-yl, substituents which may be mentioned preferably being $C_1$–$C_4$-alkyl, $C_1$–$C_4$-alkoxy and halogen, such as, for example, methyl, methoxy and chlorine;

A, Z, X E and n have the meaning given above.

The following compounds may be mentioned specifically:

3-[(6-chloro-3-pyridinyl)methyl]-N-nitro-2-thiazoleidin-imine;

1-[(6-chloro-3-pyridinyl)methyl]-N-nitro-2-piperidine-imine;

1-[(6-chloro-3-pyridinyl)methyl]-4,5-dihydro-1H-imidazole-cyanamide;

2-chloro-5-[(2-nitromethylene-1-imidazolidinyl)methyl]-pyridine;

N-[(6-chloro-3-pyridinyl)methyl]-N,N',N'-trimethyl-N'''-nitro-guanidine;

N-[(6-chloro-3-pyridinyl)methyl]-N'-cyano-N-methyl-ethaneimidamide;

1-[(6-chloro-3-pyridinyl)methyl]-tetrahydro-3,5-dimethyl-N-nitro- 1,3,5-triazine-2(1H)-imine;

N-[(6-chloro-3-pyridinyl)methyl]-N-ethyl-N'-methyl-2-nitro- 1,1-ethenediamine;

tetrahydro-2-nitromethylene-2H-1,3-thiazine;

1-(2-methylenethioethyl)-2-nitromethylene-imidazolidine.

The nitromethylenes which can be used according to the invention are disclosed in the following publications:

European Laid-Open Specification Nos. 464 830, 428 941, 425 978, 386 565, 383,091, 375 906, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389;

German Offenlegungschrift Nos. 3 639 877, 3 712 306;

Japanese Laid-Open Specification Nos. 03 220 176, 02 207 083, 63 307 857, 63 287 764, 03 246 283, 04 9371, 03 279 359, 03 255 072;

U.S. Pat. Nos. 5,034,524, 4,948,798, 4,918,086, 5,039, 686, 5,034,404;

PCT Application Nos. WO 91/17 659, 91/4965;

French Application No. 2 611 114;

Brazilian Application No. 88 03 621.

Reference is expressly made hereby to the generic formulae and definitions described in these publications and to the individual compounds described therein.

The effect on nicotinergic receptors of the central nervous system is determined by a generally customary standard method for receptor binding studies (E. C. Hulme, Editor, Receptor-Ligand Interactions, Oxford University Press, 1992, pp 1–458). The binding was measured here by displacement of [$^3$H]-cytisine by the active compounds in the rat brain membrane preparation.

Rats were sacrificed by decapitation and the entire brain was then removed immediately and processed. All following steps were carried out with cooling to 4° C. The brain was homogenized in sucrose solution (110 g of sucrose/l; 20 ml of solution per 1 g of brain mass) with the aid of a mixer. Coarse constituents were removed by centrifugation of the homogenate for 10 min at 1200 g and subsequent filtration through 5 layers of muslin. The suspension which remained (called homogenate in the following) was frozen and stored at −20° C. until use.

Buffer A for the test batch: 100 mM $K_2HPO_4/KH_2PO_4$, pH 7.4, containing 1 g/ of bovine serum albumin.

For the determination of the displacement of [$^3$H]-cytisine by the active compounds the following batch (1 ml total volume) was mixed together: 250 µl of thawed homogenate, 600 µl of buffer, 100 µl of active compound solution in buffer A (containing a concentration series in dilution steps with a factor of 10 between a maximum of $10^{-2}$M and a minimum of $10^{-10}$M of active compound, and 2 µl of methanol, from a concentrated stock solution of the active compounds), 50 µl of ($^3$H)-cytisine solution in buffer A (containing 1.48 pmol of ($^3$H)-cytisine, corresponding to 1.67 KBq, and 5 µl of ethanol, from a concentrated stock solution). In controls which contained no homogenate or no active compound, the missing volume was replaced by buffer A.

The batches were incubated at 22° C. in a shaking water bath for 60 min. To end incubation of the batches, 3 ml of ice-cold buffer A was added in each case and the whole solution was rapidly filtered through GF/C glass fibre filters. The filters were premoistened with a 1% strength solution of Prosil in buffer A. The filters were also washed twice with 3 ml of ice-cold buffer A each time. The filters were then removed and the radioactivity bound to the filters was determined in a liquid scintillation apparatus after addition of 10 ml of suitable scintillation cocktail.

All values were determined in duplicate and averaged. The concentration of active compound which leads to a 50% displacement of the specifically bound [$^3$H]-cytisine was calculated from the concentration series by a logit transformation or by the 4-parameter logistic model (T. Chard; An Introduction to Radioimmunoassay and Related Techniques; Elsevier, Amsterdam, 1990; pp 613–171; statistical assessment by computer). The negative common logarithm of this concentration is called the $pI_{50}$ in the following.

TABLE 1

Nicotine receptor [$^3$H]-cytisine displacement of compounds of the general formula (I)

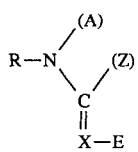

| Example No. | Structure | $pI_{30}$ |
|---|---|---|
| 1 | (structure) | 6.6 |
| 2 | (structure) | 5.3 |
| 3 | (structure) | 6.5 |

TABLE 1-continued
Nicotine receptor [³H]-cytisine displacement of compounds of the general formula (I)
$$R-N\begin{smallmatrix}(A)\\(Z)\end{smallmatrix}C=X-E \quad (I)$$
| Example No. | Structure | $pI_{30}$ |
|---|---|---|
| 4 | 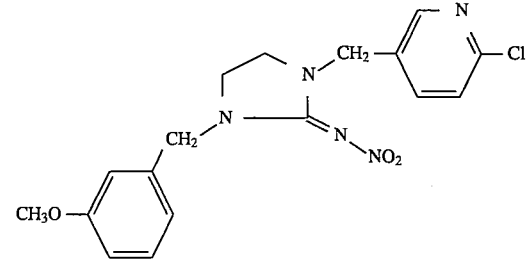 | 5.1 |
| 5 | 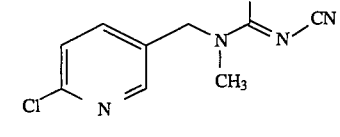 | 6.2 |
| 6 | 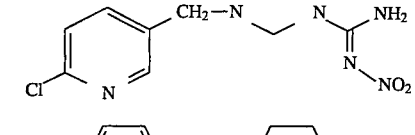 | 4.8 |
| 7 | 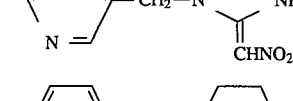 | 5.9 |
| 8 | 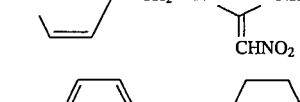 | 4.6 |
| 9 | 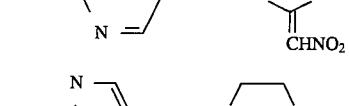 | 6.4 |
| 10 | 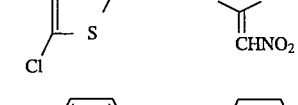 | 6.2 |
| 11 | 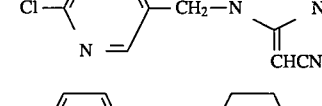 | 5.8 |
| 12 | 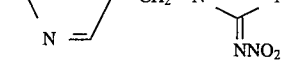 | 5.7 |

TABLE 1-continued

Nicotine receptor [$^3$H]-cytisine displacement of compounds of the general formula (I)

$$R-N\begin{matrix} (A) \\ (Z) \\ C \\ \| \\ X-E \end{matrix} \quad (I)$$

| Example No. | Structure | pI$_{30}$ |
|---|---|---|
| 13 | Cl-pyridyl-CH$_2$-N-pyrrolidine=CHCN | 6.6 |
| 14 | Cl-pyridyl-CH$_2$-N-morpholine=CHNO$_2$ | 6.4 |
| 15 | Cl-pyridyl-CH$_2$-N-piperazine(N-CH$_3$, N-CH$_3$)=NNO$_2$ | 5.2 |
| 16 | HN-imidazoline-N(pyridyl-Cl)=CH-NO$_2$ | 4.6 |

The activity of the substituted amines on learning and memory processes was investigated in the "active avoidance test". In this aversion-motivated test, rats have to learn to change to the other side of a Shuttle-box consisting of two compartments (Coulbourn Instruments) as soon as a conditioned stimulus is presented. The conditioned stimulus consists of the simultaneous sounding of an acoustic signal and the illumination of a lamp. If the rat does not leave the compartment of the Shuttle-box within 6 seconds after the start of the stimulus, it receives a slight electrical shock (0.5 mA) through the floor grating of the shuttle box. The acquisition of the active avoidance behaviour is recorded over 50 conditioning experiments. The individual experiments are separated from one another by variable rest intervals of 20–60 seconds. The increase in correct avoidance actions in the course of the training is used as a measure of the learning activity of the animals.

To detect substance effects on the learning curve (represented by the 5 average values of 10 successive conditioning experiments each), adult male rats are treated with test substances 30 minutes before the first test. Controls receive a suitable amount of the vehicle. The test results show that the compounds described can positively affect the learning behaviour of the animals.

The activity of the substituted amines described in the treatment and prevention of affective disorders is confirmed with the aid of the "rat forced swimming test". This behavioural model was described for the first time by R. D. Porsolt et al. (Nature 266; 730, 1977) and today is a generally recognized in-vivo screening model for the discovery of new antidepressants. It is based on the observation that rats in a hopeless situation remain in an immobile position ("behavioural despair"). In a preliminary test, young adult rats (3–4 months old) are placed individually for 20 minutes in glass cylinders (height 40 cm, diameter 20 cm) which are filled with water to a height of 15 cm. 24 hours after this preliminary test, the animals are again transferred to the cylinders and the period of immobility is measured over a space of time of 5 minutes.

The substituted amines described are administered in the time interval between the two swimming tests. Controls receive the vehicle.

| Test results | |
|---|---|
| Ex. No. | ED$_{50}$ [mg/kg p.o.] |
| 3 | 4.1 |
| 10 | 1.5 |
| 12 | 2.5 |

Analogously to the clinically active antidepressants described in the literature, the nitromethylenes described reduce the period of immobility and lead to behavioural activation.

On the basis of the results from the behavioural testing, the compounds described are suitable for both the therapeutic and for the preparative treatment of cognitive disorders generally, in particular of dementias of the Alzheimer type, as well as of depressions.

The invention likewise includes pharmaceutical compositions which contain the compounds mentioned in an effective amount, and their preparation and use for the treatment and prevention of the abovementioned diseases.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, it optionally being possible e.g. to use organic solvents as auxiliary solvents if water is used as a diluent.

Administration is carried out in a customary manner, preferably orally or parenterally, in particular perlingually or intravenously. Administration can also be carried out transdermally, e.g. by means of plasters.

In the case of parenteral admininstration, solutions of the active compound can be employed using suitable liquid excipients.

In general, it has proven advantageous in the case of intravenous administration to administer amounts of about 0.001 to 1 mg/kg, preferably about 0.01 to 0.5 mg/kg of body weight to achieve effective results, and in the case of oral administration the dose is about 0.01 to 20 mg/kg, preferably 0.1 to 10 mg/kg of body weight.

In spite of this, it may be necessary in some cases to depart from the amounts mentioned, namely depending on the body weight or on the type of application route, on the individual behaviour towards the medicament, the manner of its formulation and the time or interval at which administration takes place. Thus, in some cases it may be adequate to manage with less than the abovementioned minimum amount, while in other cases the upper limit mentioned has to be exceeded. In the case of the administration of relatively large amounts, it may be advisable to divide these into several individual doses over the course of the day.

We claim:

1. A method of treating or preventing brain functional disorders in a patient in need thereof which comprises administering to such patient an amount effective therefor of a compound of the formula $$R-N\diagdown_C^{(A)}\diagup^{(Z)} \quad (I)$$
$$\parallel$$
$$X-E$$

in which

R is hydrogen, or an optionally substituted acyl, alkyl, aryl, aralkyl, heteroaryl or heteroarylalkyl radical, A is hydrogen or an acyl, alkyl or aryl radical, or is a bifunctional radical which is linked to the radical Z, E is an electron-withdrawing radical, X is a —CH= or =N— radical, it being possible for the —CH= radical to be linked to the Z radical instead of an H atom, Z is an alkyl, —O—R, —S—R or $$-N\diagup^R_R$$

radical or is a bifunctional radical which is linked to the A radical or the X radical.

2. The method according to claim 1, in which

R is hydrogen, or an optionally substituted acyl, alkyl, aryl, aralkyl, heteroaryl or heteroarylalkyl radical, A is hydrogen, an optionally substituted acyl, aryl or alkyl radical, or an optionally substituted alkylene radical linked to the radical Z, E is an electron-withdrawing radical, X is a —CH= or —N= radical, Z is an optionally substituted alkyl, —OR, —SR or —NRR radical, or Z together with the atom to which it is bonded and the =C— radical in place of X, can form a saturated or unsaturated heterocyclic ring.

3. The method according to claim 1, in which

R is $R^1$—$(CH_2)_n$—, $R^1$ is optionally substituted pyridin-3-yl, and n is 1 or 2.

4. The method according to claim 1, in which

R is $R^1$—$(CH_2)_n$—, $R^2$ is optionally substituted 1,3-thiazol-5-yl, and n is 1 or 2.

5. The method according to claim 1, wherein such compound is 3-[(6-chloro-3-pyridinyl)methyl]-N-nitro-2-thiazole-idinimine.

6. The method according to claim 1, wherein such compound is 1-[(6-chloro-3-pyridinyl)methyl]-N-nitro-2-piperidineimine.

7. The method according to claim 1, wherein such compound is 1-[(6-chloro-3-pyridinyl)methyl]-4,5-dihydro-1H-imidazole-cyanamide.

8. The method according to claim 1, wherein such compound is 2-chloro-5-[(2-nitromethylene-1-imidazolidinyl)-methyl]-pyridine.

9. The method according to claim 1, wherein such compound is N-[(6-chloro-3-pyridinyl)methyl]-N,N',N'-trimethyl-N''-nitro-guanidine.

10. The method according to claim 1, wherein such compound is N-[(6-chloro-3-pyridinyl)methyl]-N'-cyano-N-methyl-ethaneimidamide.

11. The method according to claim 1, wherein such compound is 1-[(6-chloro-3-pyridinyl)methyl]-tetrahydro-3,5-dimethyl-N-nitro- 1,3,5-triazine-2(1H)-imine.

12. The method according to claim 1, wherein such compound is N-[(6-chloro-3-pyridinyl)methyl]-N-ethyl-N'-methyl-2-nitro- 1,1-ethenediamine.

13. The method according to claim 1, wherein such compound is 1-(2-methylenethioethyl)-2-nitromethylene-imidazolidine.

* * * * *

UNITED STATES PATENT AND TRADEMARK OFFICE
CERTIFICATE OF CORRECTION

PATENT NO. : 5,547,965
DATED : August 20, 1996
INVENTOR(S) : Kruger, et al.

It is certified that error appears in the above-indentified patent and that said Letters Patent is hereby corrected as shown below:

Col. 12, line 23   Delete " =C- " and substitute
                   -- $=\overset{|}{C}-$ --

Signed and Sealed this

Eleventh Day of February, 1997

*Attest:*

BRUCE LEHMAN

*Attesting Officer*  *Commissioner of Patents and Trademarks*